(12) United States Patent
Lee et al.

(10) Patent No.: US 10,149,780 B2
(45) Date of Patent: Dec. 11, 2018

(54) COMPRESSION UNDERGARMENT FOR RELIEF OF MENSTRUAL PAIN AND RELATED METHOD OF USE

(75) Inventors: Stephen D. Lee, Sarasota, FL (US); Glenn Akhavein, Bradenton, FL (US); Robert Brady, Sarasota, FL (US); Daniel Dugas, Sarasota, FL (US)

(73) Assignee: ZIIVAA IP, LLC, Sarasota, FL (US)

( * ) Notice: Subject to any disclaimer, the term of this patent is extended or adjusted under 35 U.S.C. 154(b) by 502 days.

(21) Appl. No.: 12/898,996

(22) Filed: Oct. 6, 2010

(65) Prior Publication Data
US 2011/0041839 A1 Feb. 24, 2011

Related U.S. Application Data

(63) Continuation-in-part of application No. 12/824,789, filed on Jun. 28, 2010, now Pat. No. 8,191,550, and a continuation-in-part of application No. 12/404,655, filed on Mar. 16, 2009, now Pat. No. 8,156,932, and a continuation-in-part of application No. 11/753,562, filed on May 24, 2007, now abandoned.

(51) Int. Cl.
*A61F 5/01* (2006.01)
*A61F 5/30* (2006.01)

(52) U.S. Cl.
CPC .............. *A61F 5/0193* (2013.01); *A61F 5/30* (2013.01); *A61F 2005/0183* (2013.01)

(58) Field of Classification Search
USPC .............. 2/464, 414, 319; 602/19; 128/99.1, 128/101.1, 106.1, 107.1, 108.1, 112.1
See application file for complete search history.

(56) References Cited

U.S. PATENT DOCUMENTS

| | | |
|---|---|---|
| 35,038 A | 4/1862 | Pierce |
| 264,449 A | 9/1882 | Fahs |
| 1,600,178 A | 9/1926 | Hussey |
| 2,018,981 A | 10/1935 | Tietjen |
| D99,529 S | 5/1936 | Spanel |
| D134,791 S | 1/1943 | Selver |

(Continued)

FOREIGN PATENT DOCUMENTS

WO 0041656 7/2000

*Primary Examiner* — Ophelia A Hawthorne
(74) *Attorney, Agent, or Firm* — Allen Dyer Doppelt & Gilchrist

(57) ABSTRACT

A compression undergarment to relief the symptoms of menstrual cramping may comprise a first and second pad both capable of conforming to a female user's hips. Each pad is tapered having two part construction. Such construction may include a pliable exterior panel of resilient material and an interior panel made of compressible material. The second component of the apparatus is a compression undergarment having a first and corresponding second annular sleeve. Such compression undergarment includes a front side, back side, first leg portion and second leg portion, such that positioned above the first leg portion and second leg portion is a top portion which connects both leg portions. The compression undergarment also includes a first annular sleeve capable of receiving the first pad and the second annual sleeve capable of receiving the second pad. The third component is a compression band that fits around both pads and the compression undergarment.

19 Claims, 10 Drawing Sheets

(56) References Cited

U.S. PATENT DOCUMENTS

| | | | |
|---|---|---|---|
| 2,453,370 A | 11/1948 | Hittenberger | |
| 2,493,406 A | 1/1950 | Hicks, III | |
| 2,497,443 A * | 2/1950 | Eatman | 607/108 |
| 2,552,475 A | 5/1951 | Austlid | |
| 2,590,212 A | 3/1952 | Samuels | |
| 2,652,051 A | 9/1953 | Hoover | |
| 2,654,366 A | 10/1953 | Miller | |
| 2,813,526 A | 11/1957 | Beebe | |
| 2,828,737 A | 4/1958 | Hale | |
| 3,071,133 A | 1/1963 | Eisen | |
| 3,351,053 A | 11/1967 | Stuttle | |
| 3,393,674 A | 7/1968 | Nelkin | |
| 3,396,264 A | 8/1968 | Murphy et al. | |
| 3,500,014 A | 3/1970 | Longo | |
| 3,501,616 A | 3/1970 | Arron | |
| 3,518,995 A | 7/1970 | Claff | |
| 3,532,090 A | 10/1970 | Ward et al. | |
| 3,548,817 A | 12/1970 | Mittasch | |
| 3,577,986 A | 5/1971 | Regent | |
| 3,680,563 A | 8/1972 | Forrest | |
| 3,797,501 A | 3/1974 | Di Tullio | |
| 4,122,552 A | 10/1978 | Tedford | |
| D258,770 S | 4/1981 | Stern | |
| 4,577,622 A | 3/1986 | Jennings | |
| 4,580,555 A | 4/1986 | Coppess | |
| 4,596,253 A | 6/1986 | Griffith | |
| 4,622,957 A | 11/1986 | Curlee | |
| 4,628,930 A | 12/1986 | Williams | |
| 4,671,264 A | 6/1987 | Frangi | |
| 4,675,918 A | 6/1987 | O'Brien | |
| 4,681,113 A | 7/1987 | Coplans | |
| 4,696,291 A | 9/1987 | Tyo | |
| 4,715,364 A | 12/1987 | Noguchi | |
| 4,912,813 A | 4/1990 | Muller et al. | |
| 4,937,887 A | 7/1990 | Schreiner | |
| 4,957,105 A | 9/1990 | Kurth | |
| 4,993,409 A | 2/1991 | Grim | |
| 5,129,647 A | 7/1992 | Castellanos | |
| 5,363,863 A | 11/1994 | Lelli et al. | |
| 5,383,893 A | 1/1995 | Daneshvar | |
| 5,383,920 A * | 1/1995 | Sikes | 607/112 |
| 5,388,274 A | 2/1995 | Glover et al. | |
| 5,407,422 A | 4/1995 | Matthijs et al. | |
| 5,437,618 A | 8/1995 | Sikes | |
| 5,476,492 A | 12/1995 | Unrug | |
| 5,486,680 A | 1/1996 | Lieberman | |
| 5,528,775 A | 6/1996 | Marenda | |
| 5,551,093 A | 9/1996 | Stricker | |
| 5,588,186 A | 12/1996 | Ko | |
| 5,628,721 A | 5/1997 | Arnold et al. | |
| D380,051 S | 6/1997 | Davis et al. | |
| 5,636,377 A * | 6/1997 | Wiener | 2/465 |
| 5,647,824 A | 7/1997 | Levenson | |
| 5,690,122 A | 11/1997 | Weber-Unger | |
| 5,701,608 A | 12/1997 | Kohn | |
| 5,728,055 A | 3/1998 | Sebastian | |
| 5,758,367 A | 6/1998 | Torrent Lopez et al. | |
| 5,782,781 A | 7/1998 | Nagaoka | |
| 5,799,650 A | 9/1998 | Harris | |
| 5,817,145 A | 10/1998 | Augustine et al. | |
| 5,830,168 A | 11/1998 | Finnell et al. | |
| 5,893,368 A | 4/1999 | Sugerman | |
| 5,913,410 A | 6/1999 | Tsuchiya | |
| 5,947,914 A | 9/1999 | Augustine | |
| 5,954,680 A | 9/1999 | Augustine | |
| 5,964,721 A | 10/1999 | Augustine | |
| 5,964,723 A | 10/1999 | Augustine | |
| 5,986,163 A | 11/1999 | Augustine | |
| 6,010,527 A | 1/2000 | Augustine et al. | |
| 6,013,097 A | 1/2000 | Augustine et al. | |
| 6,045,518 A | 4/2000 | Augustine | |
| 6,065,166 A | 5/2000 | Sharrock et al. | |
| 6,066,109 A | 5/2000 | Buser et al. | |
| 6,071,254 A | 6/2000 | Augustine | |
| 6,093,160 A | 7/2000 | Augustine et al. | |
| 6,099,490 A | 8/2000 | Turtzo | |
| 6,110,197 A | 8/2000 | Augustine et al. | |
| 6,149,497 A | 11/2000 | Smith | |
| 6,213,966 B1 | 4/2001 | Augustine | |
| 6,217,535 B1 | 4/2001 | Augustine | |
| 6,235,049 B1 | 5/2001 | Nazerian | |
| 6,241,693 B1 | 6/2001 | Lambden | |
| 6,241,697 B1 | 6/2001 | Augustine | |
| 6,248,084 B1 | 6/2001 | Augustine et al. | |
| 6,264,622 B1 | 7/2001 | Augustine | |
| 6,267,740 B1 | 7/2001 | Augustine et al. | |
| 6,293,917 B1 | 9/2001 | Augustine et al. | |
| 6,328,627 B1 | 12/2001 | Smith | |
| 6,347,413 B1 * | 2/2002 | Sciscente et al. | 2/465 |
| 6,406,448 B1 | 6/2002 | Augustine | |
| 6,407,307 B1 | 6/2002 | Augustine | |
| 6,419,651 B1 | 7/2002 | Augustine | |
| 6,423,018 B1 | 7/2002 | Augustine | |
| 6,454,628 B1 * | 9/2002 | Shunichirou | A41C 1/003 128/96.1 |
| 6,460,195 B2 | 10/2002 | Wang | |
| 6,465,708 B1 | 10/2002 | Augustine | |
| 6,468,295 B2 | 10/2002 | Augustine et al. | |
| 6,580,012 B1 * | 6/2003 | Augustine et al. | 602/42 |
| 6,592,428 B2 | 7/2003 | Smith | |
| 6,605,051 B2 | 8/2003 | Augustine | |
| 6,613,034 B2 | 9/2003 | Nozaki et al. | |
| 6,634,533 B2 | 10/2003 | Thompson et al. | |
| 6,709,729 B2 * | 3/2004 | Baruch | 428/101 |
| 6,783,506 B2 | 8/2004 | Seering et al. | |
| 6,820,574 B2 | 11/2004 | Sharpe | |
| 6,840,915 B2 | 1/2005 | Augustine | |
| 6,921,374 B2 | 7/2005 | Augustine | |
| 6,987,209 B2 | 1/2006 | Augustine et al. | |
| 7,008,389 B2 | 3/2006 | Krieg et al. | |
| 7,066,181 B2 | 6/2006 | West | |
| 7,122,046 B2 | 10/2006 | Augustine et al. | |
| 2005/0090882 A1 * | 4/2005 | Wei | 607/108 |
| 2005/0182344 A1 * | 8/2005 | Dixon | 602/1 |
| 2005/0251075 A1 | 11/2005 | Smith | |
| 2006/0254598 A1 | 11/2006 | Saul | |

* cited by examiner

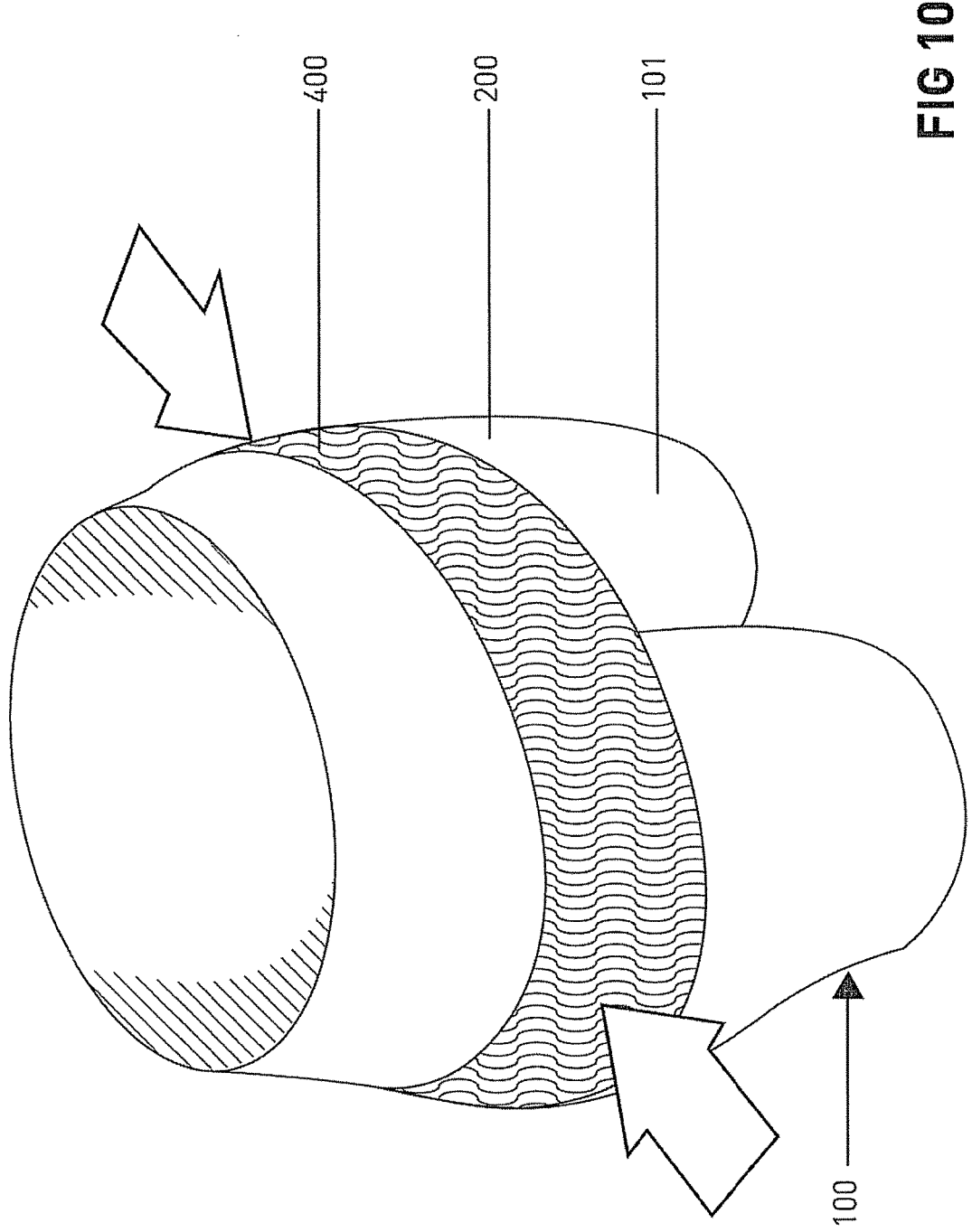

COMPRESSION UNDERGARMENT FOR RELIEF OF MENSTRUAL PAIN AND RELATED METHOD OF USE

CROSS-REFERENCE TO RELATED APPLICATIONS

This is a continuation-in-part of application Ser. No. 12/824,789 entitled "Method and Apparatus to Relieve Menstrual Pain," filed on Jun. 28, 2010, now U.S. Pat. No. 8,191,550, which in turn is a continuation-in-part of application Ser. No. 12/404,655 entitled "Method and Apparatus to Relieve Menstrual Pain" filed on Mar. 16, 2009, now U.S. Pat. No. 8,156,932, which in turn is a continuation-in-part of application Ser. No. 11/753,562 filed on May 24, 2007, now abandoned, all of which are incorporated by reference herein.

FIELD OF THE INVENTION

The present invention relates to an undergarment designed to relieve menstrual pain via compression. More specifically, the invention relates to an undergarment (and method of use) having one or more pads sufficient to apply pressure to the exterior of the female body proximate the hips.

BACKGROUND OF INVENTION

Menstrual cramping (dysmenorrheal) is a medical condition characterized by severe uterine pain during menstruation. The condition is the result of contractions of the uterus as it expels unneeded contents and also the passage of clotted blood through the cervix. The underlying pain results when the uterine muscles contract too hard or fast resulting in severe discomfort around the abdomen, back and often the legs.

The condition most commonly affects women between the ages of 20 through 24. While most women only experience minor pain during menstruation, menstrual cramps are often so severe as to limit normal activities or may require medication. Menstrual cramping may precede menstruation by several days or may accompany it. More typically, such cramping occurs on the first or second day of the menstrual cycle.

According to the United States Department of Health and Human Services, roughly 52 percent of women in the United States between the ages of 15 to 51 suffer from some level of menstrual cramps. Of these, 10 percent have such a severe condition as to require a doctor visit. Statistics from the American College of Obstetrics and Gynecology reveal that menstrual cramping represents the number one cause of missed school and work days among women. In fact, menstrual cramping accounts for an astonishing 140 million hours of lost school and work every year.

Despite these alarming statistics, very little has been done to advance the art of treating menstrual cramping. Traditional methods of chemical treatment include taking an over-the-counter pain killer which includes ibuprofen as the active ingredient. Non-traditional methods include a regiment of taking calcium, Vitamin D and magnesium supplements. Non-medicinal ways of treatment typically include use of heat around the abdomen, such as a heating pad or taking a warm sitz-bath.

Each aforementioned treatment option has its limitations, and none actually work to treat the underlying medical cause of these cramps. Studies show how increased ingestion of ibuprofen may result in multiple adverse drug reactions (ADRs), as well as associated gastrointestinal (GI) effects and renal problems. Many women cannot always take chemical medications due to these problems as well as other undesirable side affects. Dietary supplements like calcium, Vitamin D and magnesium may help reduce pain but do not eliminate or treat the condition. Use of heat around the abdomen only offers at most temporary relief and does nothing more than mask the pain.

With the growing acceptance of complementary and alternative medicine (CAD), there is a need in the art for an effective yet non-chemical treatment of menstrual cramps. This is especially true with the large number of individuals whose personal and spiritual beliefs preclude use of chemical medicines like ibuprofen.

SUMMARY OF THE INVENTION

This invention solves the current limitations in the art of alleviating menstrual cramps through an alternative and non-chemical form of treatment. As menstrual cramping occurs when the uterine muscles contract too hard or fast resulting in the various tissue connected to (or located near) the uterus to be stretched, the present invention treats the condition through counteracting this excessive stretching. Specifically, to relieve the pain and discomfort associated with menstrual cramping, the invention employs compression at or proximate to each greater trochanter—the large, irregular eminence located at the top of the femur bone—at both lateral sides of the female hips. Through compressing the area adjacent to each greater trochanter, the ligaments and tendons proximate to the uterus relax, helping alleviate the pain associated with menstrual cramps.

In the preferred embodiment of the invention, the apparatus may comprise a first pad and corresponding second pad both capable of conforming to a female user's hips. Each pad is preferably tapered (or has an elliptical or circular shape) of two part construction. Such construction may include a hard yet pliable exterior panel made of resilient material and an interior panel made of a soft and compressible material such as neoprene.

The second component of the apparatus is a compression undergarment having a first annual sleeve and corresponding second annular sleeve. Such compression undergarment may include a front side, corresponding back side, first leg portion and second leg portion, such that positioned above the first leg portion and second leg portion is a top portion which connects both leg portions. Moreover the compression undergarment may also include a first annular sleeve capable of receiving the first pad and the second annual sleeve capable of receiving the second pad.

The third component of the apparatus is a compression band of sufficient size and dimension to fit around both pads as well as the compression undergarment. Such invention further contemplates use of variable strength compression bands which create varying levels of force onto both pads which in turn squeeze the pads onto the female user's hips and accordingly treat the greater trochanters.

Optionally, each pad may include a heat therapy assembly having both a female holder and a removable male heat pad. Here, the female holder is essentially elliptical and includes an outer ring and a cavity sufficient to receive the male heat pad. Correspondingly, the male heat pad has a sufficient size and dimension to be locked within the cavity of the female holder. In addition, the male heat pad has an exterior sleeve filled with a gel or liquid capable of conducting heat.

The invention further contemplates a method of relieving the effects of menstrual cramping through use of the apparatus. The first step is to place a first pad into a first annular sleeve within a compression undergarment. The next step is to similarly position a second pad into a second annular sleeve of the compression undergarment. As a third step, the method contemplates securing one or more compression belts over both pads and the compression undergarment. Finally, the method contemplates fitting the compression under garment onto the female user such that the first pad and the second pad are positioned proximate the greater trochanters.

BRIEF DESCRIPTION OF THE DRAWINGS

For a fuller understanding of the invention, reference is made to the following detailed description, taken in connection with the accompanying drawings illustrating various embodiments of the present invention, in which:

FIG. 10 illustrates an all-in-one apparatus having an integral compression band.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The present invention relates to a method and apparatus to non-chemically relieve menstrual cramping through use of compression at or proximate the greater trochanters. The typical cause of menstrual cramping is the excessive stretching of the muscles and tendons surrounding the uterus when expelling unwanted materials on the inner uterine wall during menstruation. When these muscles contract too fast or hard, it results in stretching of tissue resulting in the pain and discomfort associated with menstrual cramping.

Overall Components of the Apparatus

Figure 1:
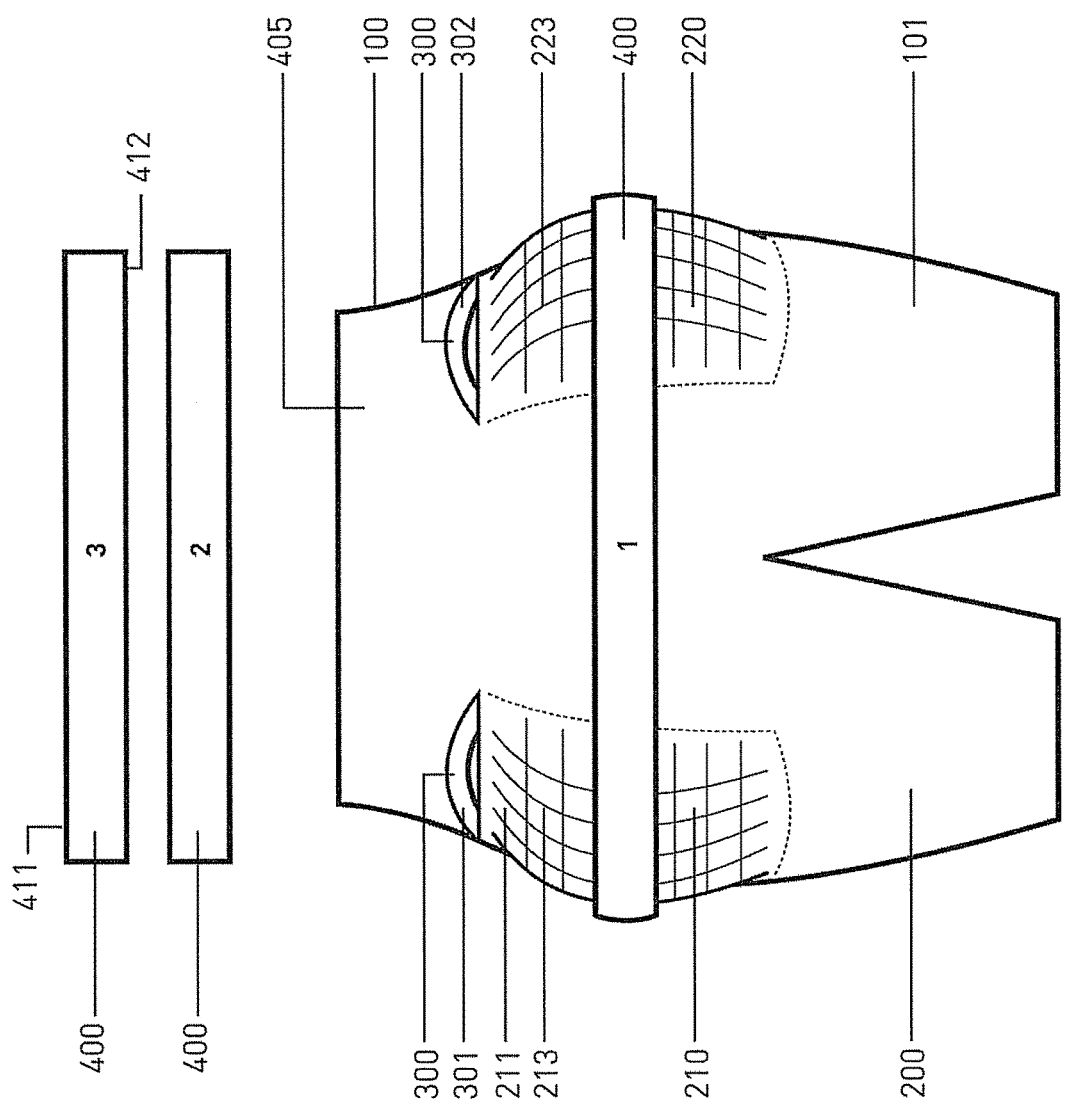
FIG. 1 is a front view of the compression undergarment showing placement of the tapered pads into the annular sleeves.

As shown and illustrated, by way of example, in FIG. 1, the invention is directed to a multi-component apparatus 100 used to create effective compression proximate the hips of a female suffering the effects of menstrual cramping. More specifically, the invention teaches use of a compression undergarment 200 worn during treatment of menstrual cramping to reduce the stretching of the muscles and tendons surrounding the uterus during menstruation. Such compression undergarment 200 is capable of securing one or more tapered pads 300 which are positioned proximate the hips. Moreover, one or more varying strength compression bands 400 having a sufficient size and dimension to surround and engage the tapered pads 300 are also used to create the necessary compression force.

As further shown in FIG. 1, the central component 101 of the apparatus 100 is the compression undergarment 200. While such device can take several shapes, it is preferable the compression undergarment 200 take the general form of a traditional pair of shorts, a tight fitting skirt, pants, or spanx. The key to such form is whether such clothing is tight fitting proximate the female user's (U) hips, if such design affords the ability to attach tapered pads 300 proximate the hips, and whether the clothing is sufficiently comfortable and discrete to be worn under traditional clothing (such as professional attire, or other related attire). This allows the ability for the apparatus 100 to be worn outside the home during normal routines—such as work and/or travel.

As a second salient component 101 of the apparatus 100, the invention contemplates use of one or more tapered pads 300. Preferably, the apparatus 100 includes a first tapered pad 301 and a corresponding second tapered pad 302 to be positioned proximate the user's hips. While the tapered pads 300 can take many a form, it is preferred that they are curved to conform to the shape and orientation of the female user's (U) hips.

It is further desired that the tapered pads 300 are made of two-part construction such that they include a resilient exterior panel 310 with a corresponding soft compressible interior panel 320. Although the invention contemplates a generally tapered shape for the pads 300, such component 101 can be any sufficient size to conform to the shape of the user's (U) hips. Examples of such shapes include tear shape, elliptical and curved tapered pads 300.

As a third salient component 101 of the apparatus 100, the invention also contemplates use of variable strength compression bands 400. Each compression band 400 has a sufficient size and dimension to fit around both the user's (U) hips, but also the compression undergarment 200. In addition, each compression band 400 is capable of exerting force onto each tapered pad 300 that is affixed to the compression undergarment 200. It is further contemplated each compression band 400 has a different level and amount of constriction—such that a user can decide and confirm what level of compression is needed to provide relief based upon the level of the menstrual cramping.

One of ordinary skill in the art, through review and study of the foregoing disclosure and figures shall recognize additional components 101 and configurations for the apparatus 100—including different orientations and functionality for the compression undergarment 200, tapered pads 300 and compression bands 400.

The Tapered Pads

Figure 2:
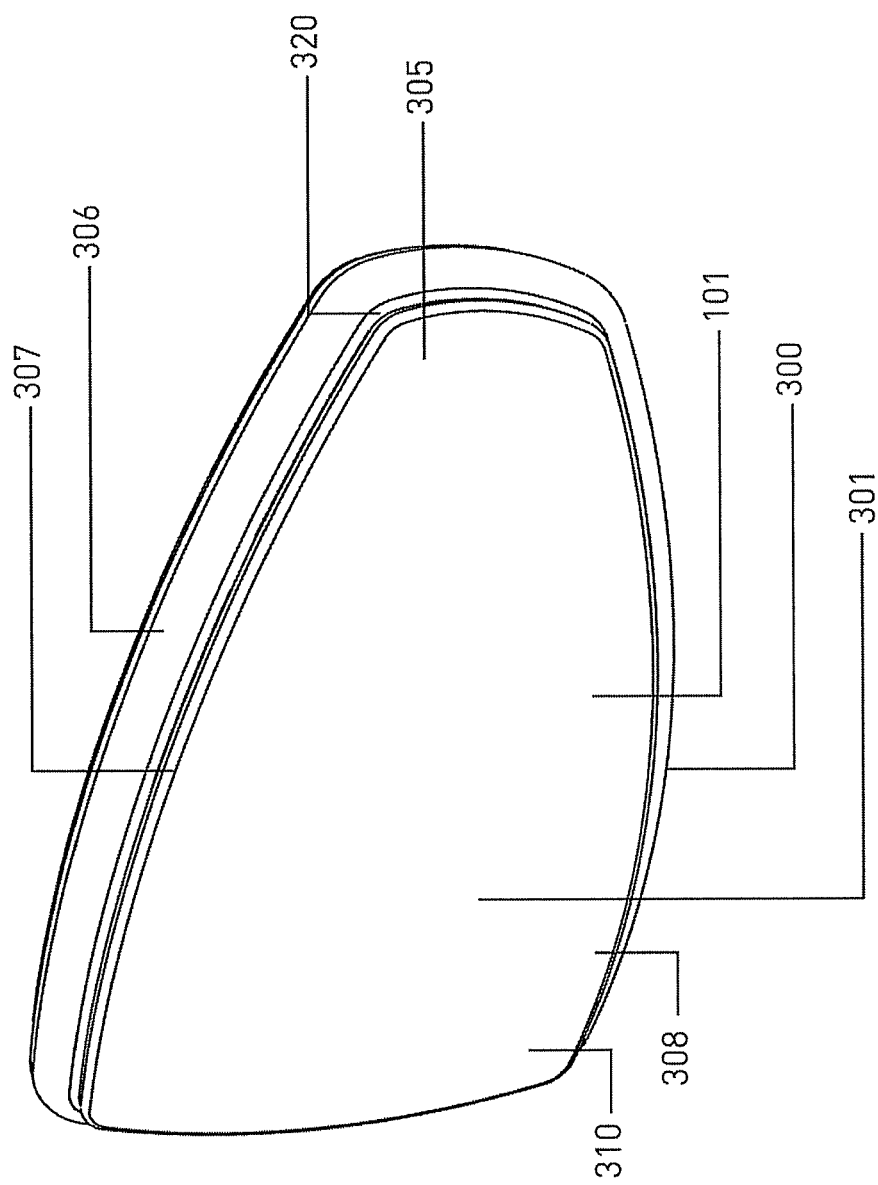
FIG. 2 is a perspective view of the components of a two-part construction tapered pad for later placement into the compression undergarment.
Figure 3:
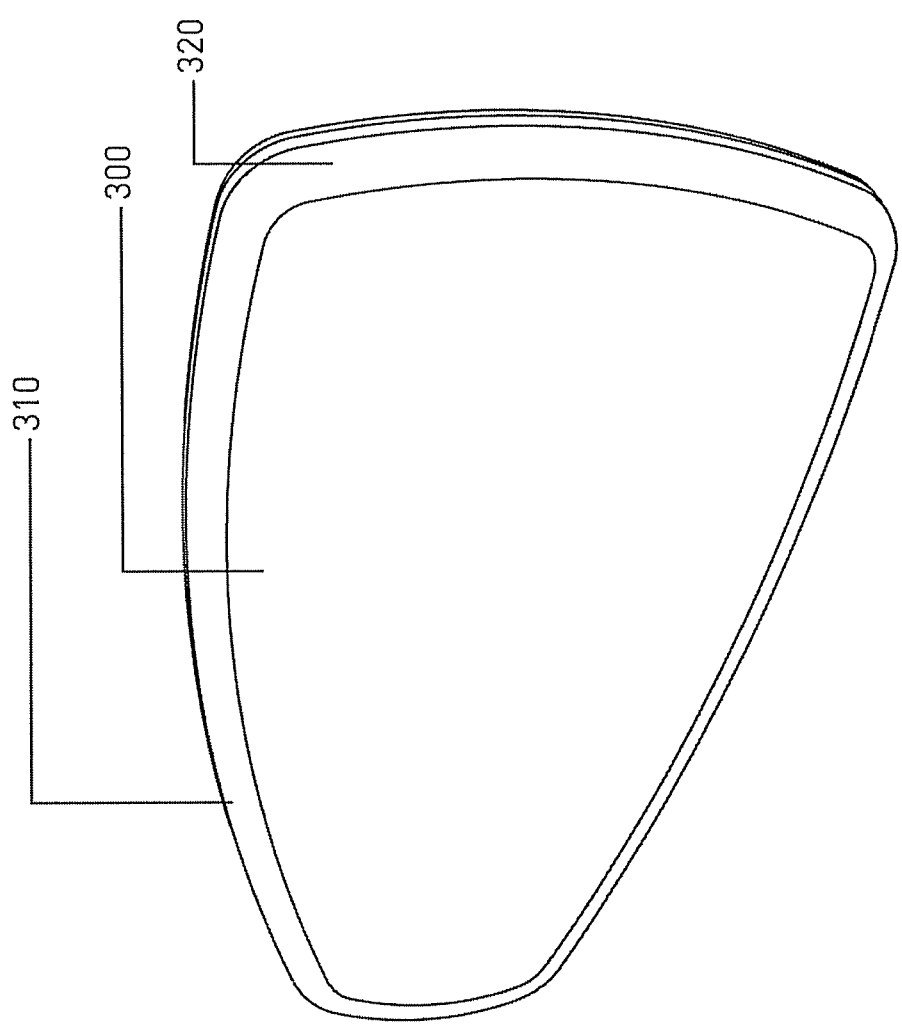
FIG. 3 is a second perspective view of the two-part construction tapered pad for later placement into the compression undergarment.
Figure 4:
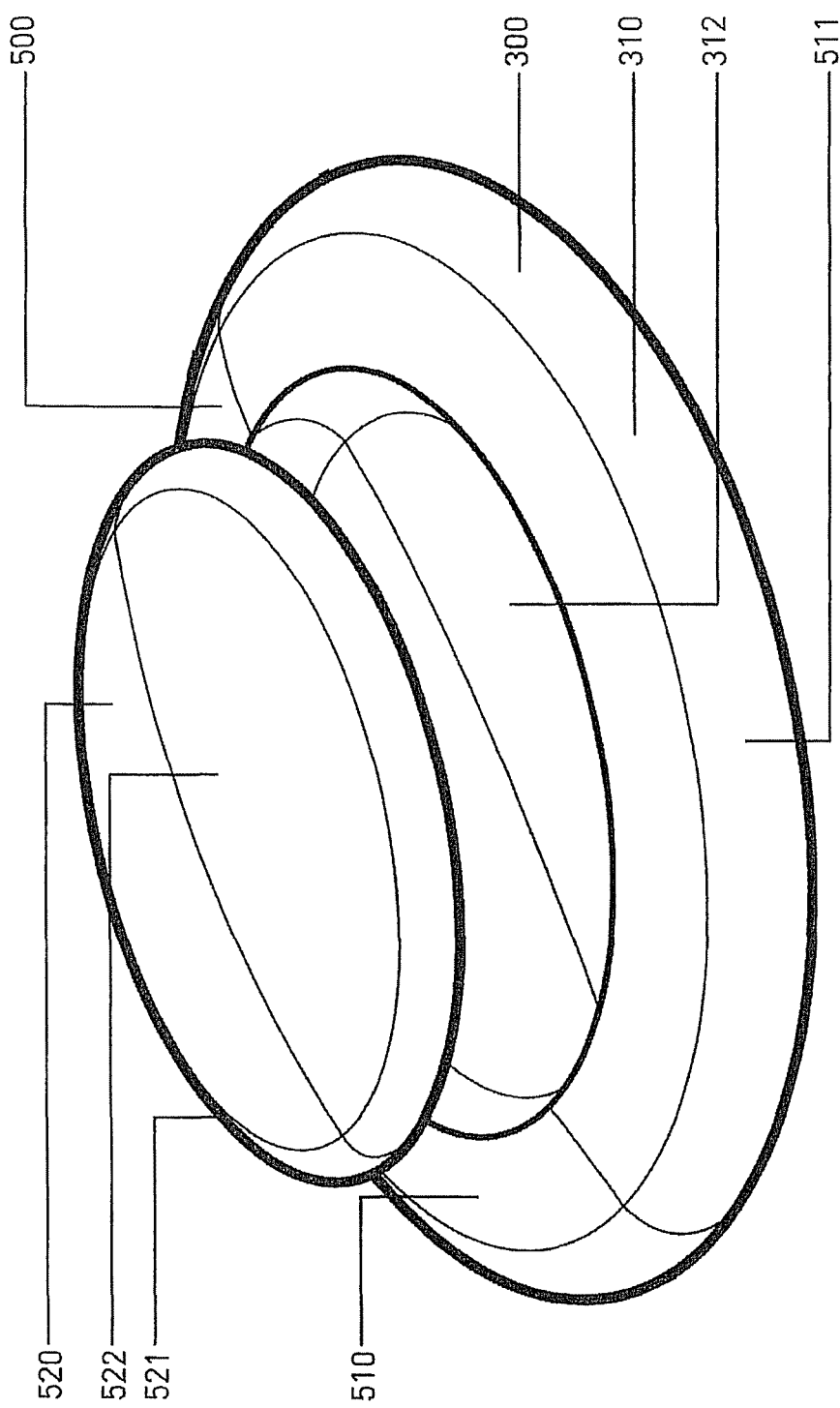
FIG. 4 is a perspective view of a heat pad assembly.

FIGS. 2 through 4 illustrate the primary shape and orientation of the tapered pads 300. Although the tapered pads 300 can vary in size, construction and functionality, they provide three primary roles within the apparatus 100. First, they serve as an intermediary component 101 between the compression undergarment 200 and each of the respective compression bands 400. Second, each tapered pad 300 focuses the force of compression at the user's hips and preferably proximate the greater trochanters to ultimately provide relief from menstrual cramping. Third, each tapered pad 300 may optionally provided additional therapy in the form of heat treatment or vibration therapy.

First turning to FIG. 2, each tapered pad 300 includes a front side 305, a corresponding rear side 306, a top side 307 and a corresponding bottom side 308. As shown, the top side 307 mirrors the size, shape and dimension of the bottom side 308. In addition, the front side 305 is preferably smaller in size compared to the rear side 306. Although the tapered pad 300 is preferably a tear drop shape, other shapes are contemplated including but not limited to elliptical and circular pad shapes.

As further illustrated in FIG. 3, each tapered pad 300 is preferably of two part construction having a resilient exterior panel 310 with a corresponding soft compressible interior panel 320. Preferably, the size and dimension of the resilient exterior panel 310 mirrors the corresponding soft compressible interior panel 320. The resilient exterior panel 310 is preferably made of a strong yet pliable material such as a plastic, lightweight metal or composite. Preferably, such resilient exterior panel 310 can be molded to conform to the unique shape of the user's (U) hips. In one contemplated embodiment, the exterior panel 310 can be heated and/or molded to create such shape.

FIG. 3 likewise illustrates the interior panel 320 of the tapered pad 300. As shown, the interior panel 320 includes a compressible material to conform the tapered pad 300 to the unique contours of the user's (U) hips. While a variety of soft and pliable materials can be used, it is preferable that the interior panel 320 is constructed of neoprene. However, any other spongy material can be used so long as it is hypoallergenic.

As previously discussed, each tapered pad 300 can optionally provide treatment in the form of heat therapy. FIG. 4 illustrates, by way of example, one embodiment of a tapered pad 300 capable of providing therapy via a heat therapy assembly 500 (which can be used to provide forms of therapy in addition to heat). Such health therapy assembly 500 includes two primary parts: a female holder 510 and a removable male heat pad 520. Such female holder 510 is preferably molded into the exterior panel 320 of the tapered pad 300. Moreover, the female holder 510 is essentially elliptical and includes an outer ring 511 and a cavity 512. Dimensions of the outer ring 511 mirror the shape of the exterior of the cavity 512.

As further shown, the male heat pad 520 is likewise elliptical and has a sufficient size and dimension to be received and then locked within the cavity 512. The male heat pad 520 includes an outer sleeve 521 as well as an inner customizable conductive core 522. The outer sleeve 521 could be made of a breathable fabric or have a disposable pad cover, while the conductive core 522 could be made of a gel or is a liquid contained within bladder. The male heat pad 520 could be placed in an oven, microwave or similar heating area to be preheated before positioning within the cavity 512.

Accordingly, it is important for the female holder 510 to allow this heat to pass through to the user (U). The male heat pad 520 could also be made of a variable density material or a specific geometry to provide a customized shape to conform to the user's (U) unique body type and hips. Such varying density of the male heat pad 520 can be configured in order to provide additional specific treatment proximate the greater trochanters.

The Compression Undergarment

Figure 5:
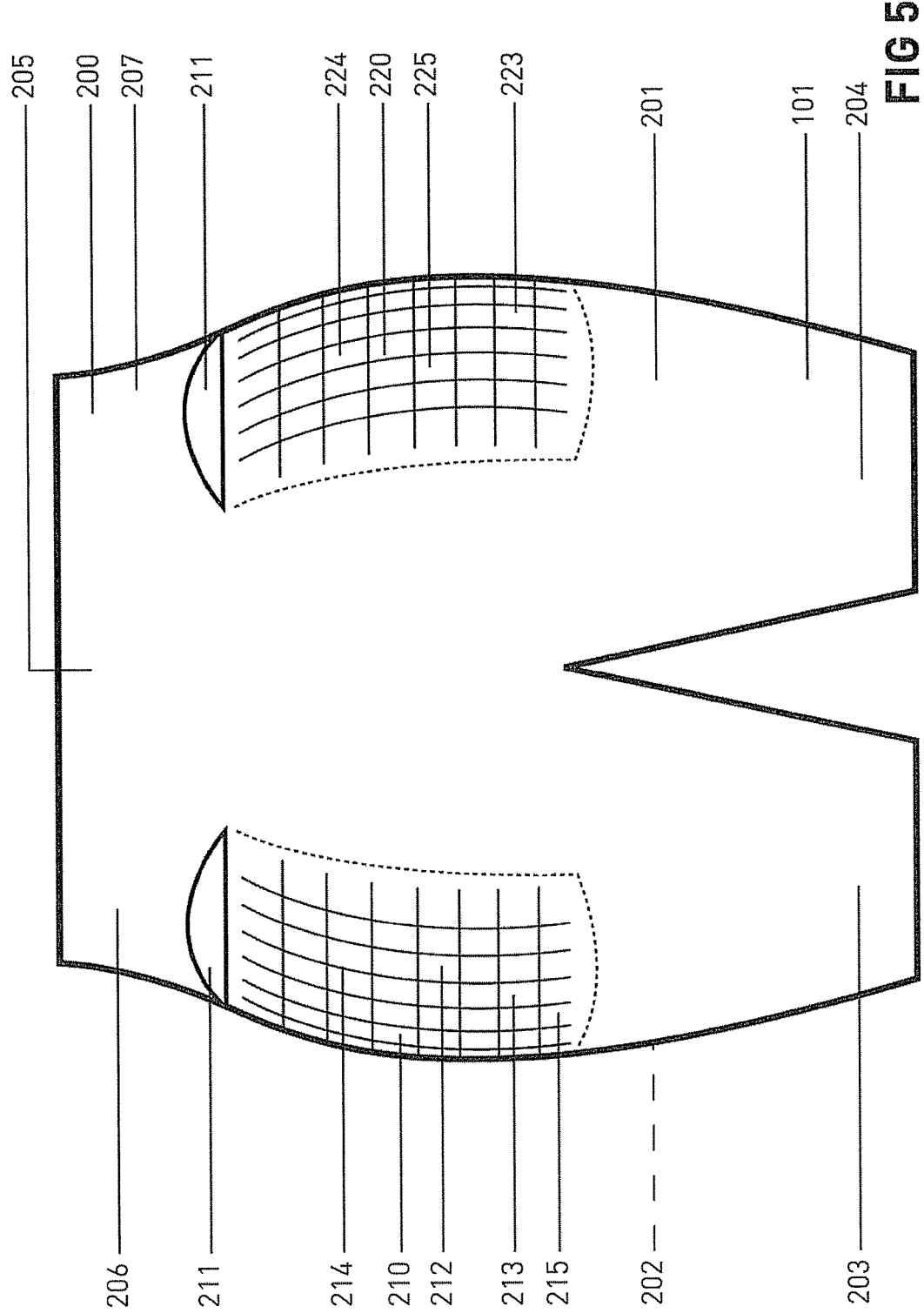
FIG. 5 is a front view showing one embodiment of the compression undergarment having a pair of annular sleeves.
Figure 6:
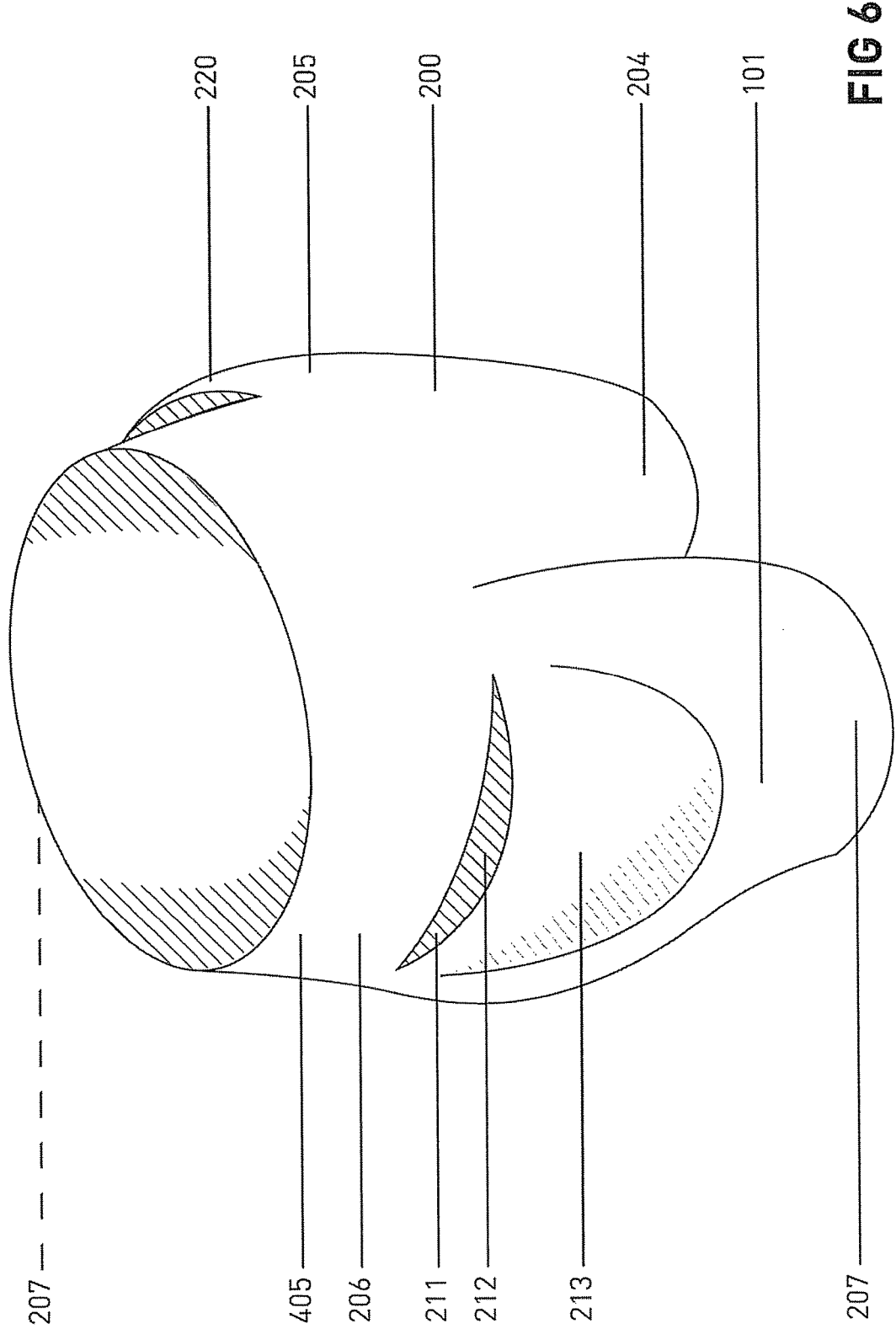
FIG. 6 is a perspective view showing the placement of two annular sleeves on the compression undergarment.

As previously discussed, the central component 101 of the apparatus 100 is the compression undergarment 200. Both FIG. 5 and FIG. 6 illustrate, by way of example, one embodiment of the compression undergarment 200. As previously discussed, such compression undergarment 200 can take the general form of a traditional commercially available pair of shorts, skirt, pants, or spanx. While such compression undergarment 200 illustrates a device that includes leggings, the invention contemplates use other forms of undergarments and intimates that do not include leg portions. One of ordinary skill in the art, upon review of both FIGS. 5 and 6 as well as the following disclosure, will understand and recognize additional types of garments which can employ the technology to provide relief from menstrual cramping.

First turning to FIG. 5, the overall compression undergarment 200 includes a front side 201, corresponding back side 202, first leg portion 203 and second leg portion 204. Positioned above the first leg portion 203 and second leg portion 204 is a top portion 205 (which connects both leg portions 203 and 204). This top portion 205 includes a first side 206 and corresponding second side 207 (which mirror each other in dimension and shape).

Positioned proximate the first side 206 of the top portion 205 is a first annular sleeve 210. The first annular sleeve 210 includes a top opening 211 and a cavity 212 which forms a first pocket 213. Such first annular sleeve 210 should be positioned along the compression undergarment 200 so as to be located proximate to one of the user's (U) greater trochanters.

A first tapered pad 301 is capable of being positioned at the top opening 211 and then inserted into the cavity 212. The first annular sleeve 210 is of a sufficient size and dimension so as to hold and maintain the shape of the first tapered pad 301. Preferably, the first tapered pad 301 is sufficiently curved and contoured so as to mirror to shape of the user's (U) hips. Moreover, the first pocket 213 of the first annular sleeve 210 is capable of holding and maintaining the curved first tapered pad 301.

Correspondingly, as shown in FIG. 5 a second annular sleeve 220 is positioned proximate the second side 207 of the top portion 205. Mirroring the structure and arrangement of the first annular sleeve 210, the second annular sleeve 220 likewise includes a top opening 211 and a cavity 212 which forms a second pocket 223. In addition, this second annular sleeve 220 should be positioned along the compression undergarment 200 so as to be located proximate the user's (U) greater trochanters.

As illustrated in FIG. 5, a second tapered pad 302 is capable of being positioned at the top opening 211 and then inserted into the cavity 212. The second annular sleeve 220 is of a sufficient size and dimension so as to hold and maintain the shape of the second tapered pad 302. Preferably, the second tapered pad 302 is sufficiently curved and contoured so as to mirror to shape of the user's (U) hips. Moreover, the pocket 216 of the second annular sleeve 220 is capable of holding and maintaining the curved second tapered pad 302 while post-treatment is administered. The area of the first annual sleeve 210 can optionally include a first set of grid lines 214, while a second set of grid lines 224 can be positioned proximate the second annular sleeve 220. Both sets of grid lines 214 and 224 may be used to assist a user (U) in properly positioning the tapered pads 301 and 302 proximate the greater trochanters.

Compression Bands

Figure 9:
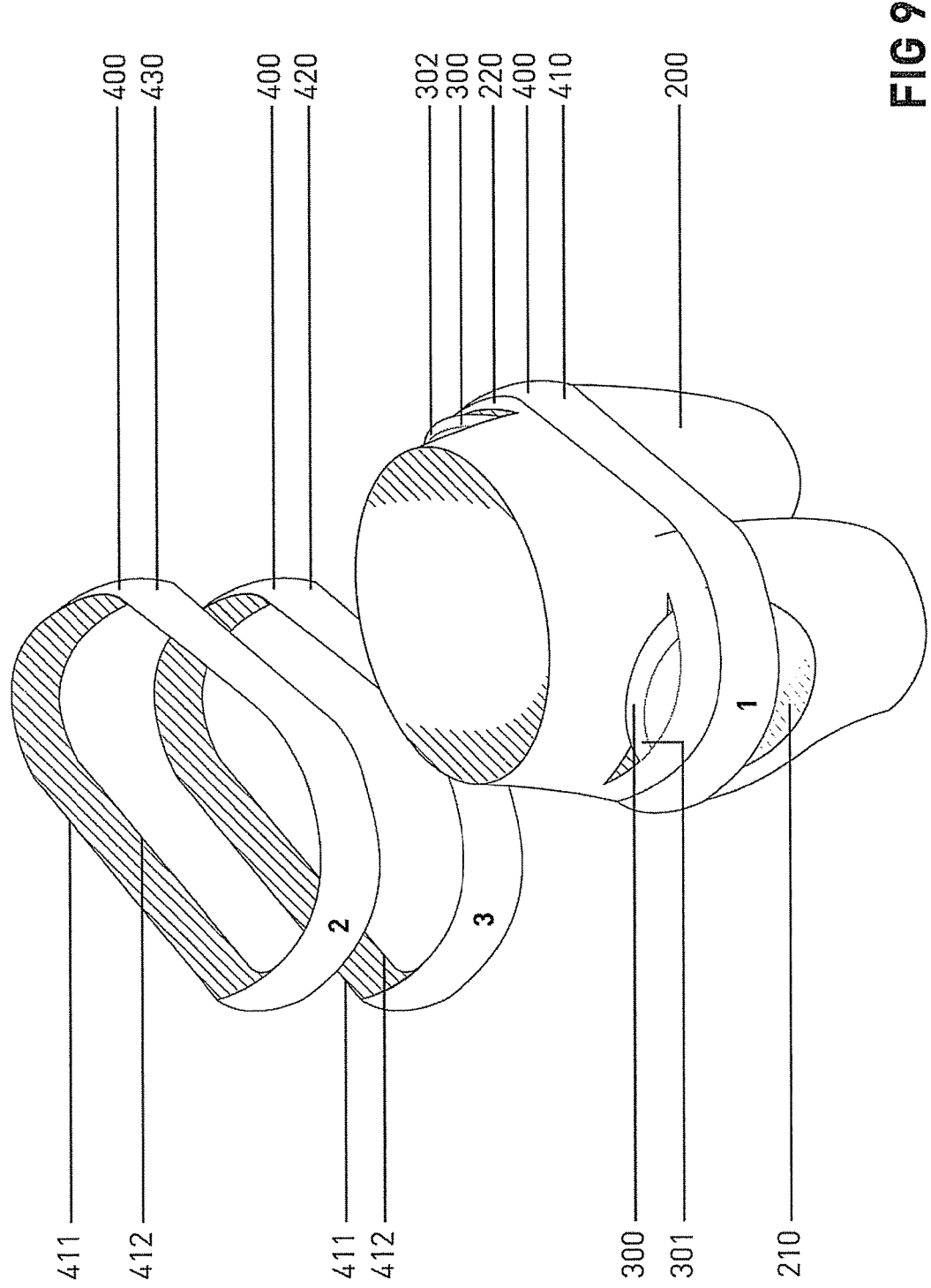
FIG. 9 is a perspective view showing positioning of compression bands proximate the two tapered pads and the compression undergarment.

FIG. 1 and FIG. 9 illustrate, by way of example the functionality and general structure for the compression bands 400. As shown in both illustrations, the apparatus 100 can include one or more compression bands 400. The compression bands 400 are a sufficient size and dimension so as to wrap around both the compression undergarment 200 as well as the both the first tapered pad 301 and second tapered pad 302 maintained within the respective annular sleeves 210 and 220. Moreover, such compression bands 400 should have a sufficient level of strength to contact the tapered pads 300 and force them onto the user's (U) hips to engage the greater trochanters.

As shown and illustrated in FIG. 1, each compression band 400 may include a top edge 411 and a corresponding bottom edge 412. Such compression band 400 is placed over the compression undergarment 200 such that it covers at least a portion of both the first annular sleeve 210 and corresponding second annular sleeve 220 (as shown in FIG. 9). In one embodiment, the top edge 411 of the compression band 400 and the bottom edge 412 should be equidistant from the vertical centerline of the tapered pad 300.

The compression band 400 can take many a form and dimension. Preferably, the compression band 400 is a single and contiguous member of uni-body construction formed of a resilient and elastic material such as synthetic rubber. However, such compression band 400 could alternatively be non-contiguous and instead include a belt like structure. Such belted compression band 400 could have a fastener to adjustment to create a specific size, girth and accordingly compression strength.

As further shown in FIG. 1, the invention also contemplates including a plurality of compression bands 400 for use with the compression undergarment 200, where each compression band 400 has a different level of elasticity and compression strength. As shown, the apparatus 100 can include a first compression band 410, a second compression band 420 and a corresponding third compression band 430—each differing in compression strength. For example, a user (U) may desire to have lower compression strength and choose a lower strength elastic compression band 410. Alternatively, a user (U) having a larger degree of menstrual cramping may desire to have a greater strength elastic compression band 430 to force each of the pads 301 and 302 onto the hips of the user (U) proximate the greater trochanters. The invention also contemplates placement of two or more compression bands 410 and 420 on the top portion 205 of the compression undergarment 200 to provide relief.

Method of Use

Figure 7:
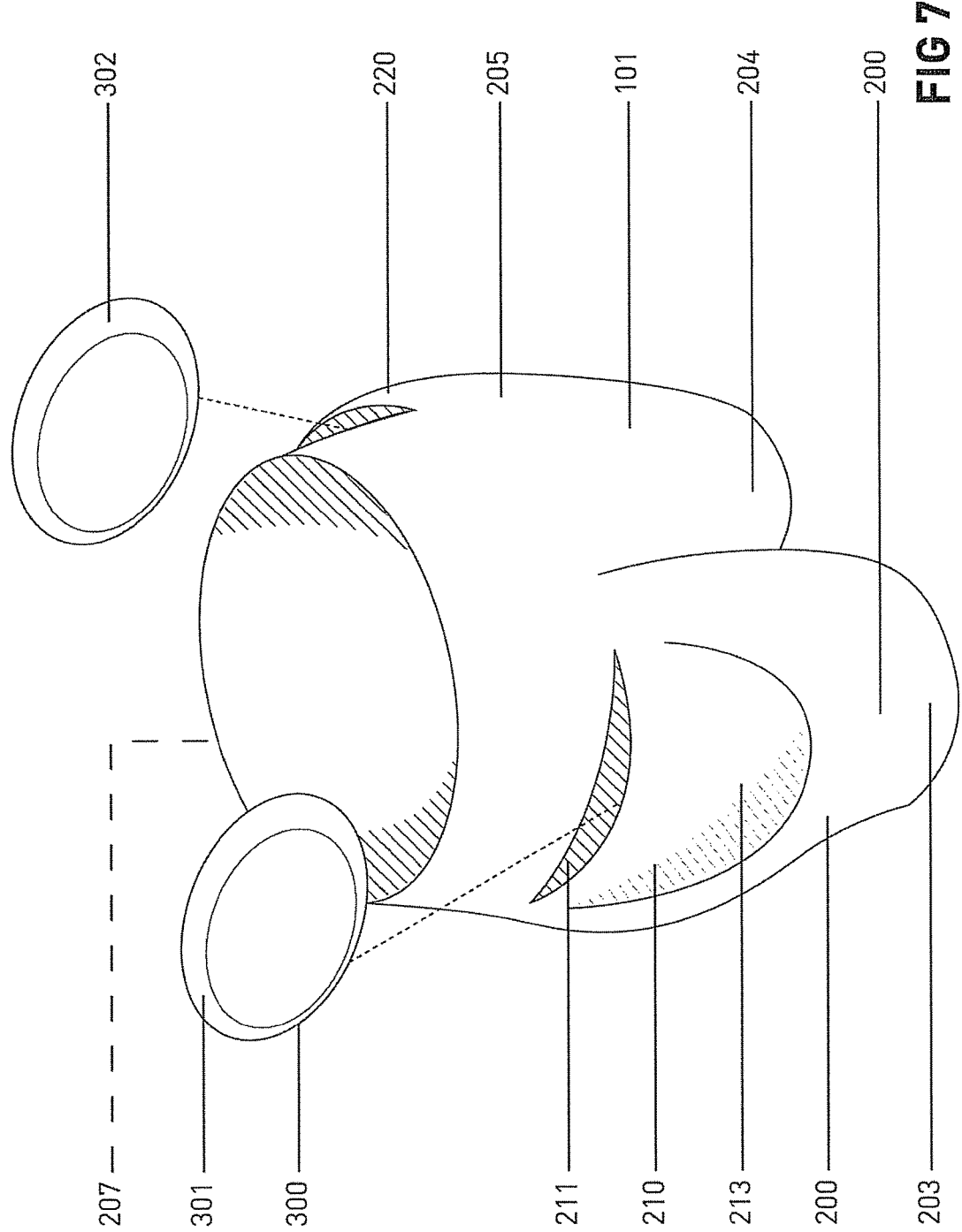
FIG. 7 is an exploded view showing two tapered pads directed towards the annular sleeves of the compression undergarment.
Figure 8:
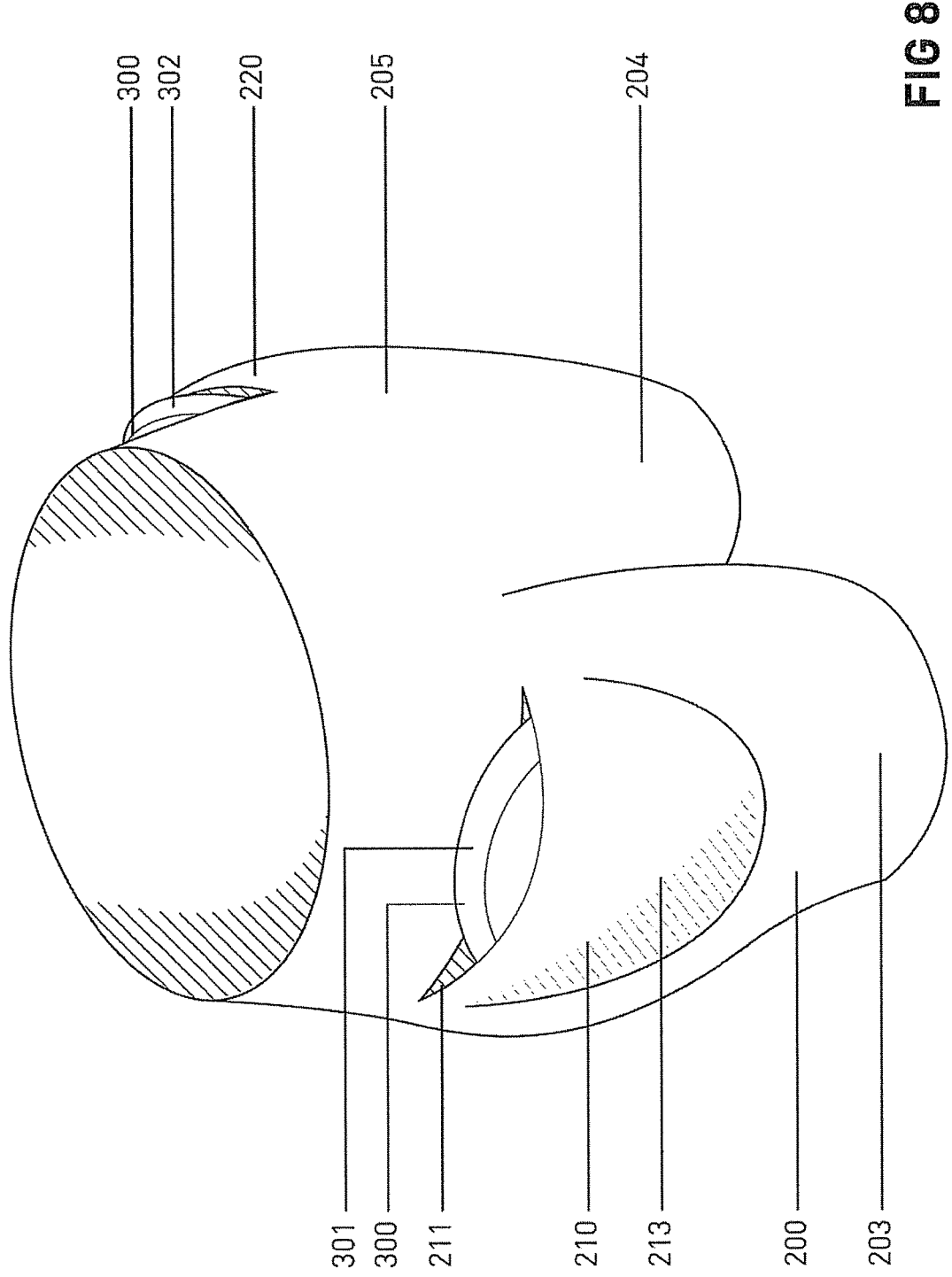
FIG. 8 is a perspective view showing placement of two tapered pads within the annular sleeves of the compression undergarment.

Based upon the structure described above, invention is also directed to a method of relieving the effects of menstrual cramping through use of the apparatus 100. The first step of the method is to place the first tapered pad 301 into the top opening 211 of the first annual sleeve 210 of the compression undergarment 200 (as shown in FIGS. 6 through 8). Correspondingly, the second step is the place the second tapered pad 302 into the top opening 211 of the corresponding second annual sleeve 220 (shown in FIG. 8). As a third step, both tapered pads 301 and 302 are positioned within each cavity 212 of the first pocket 213 and corresponding second pocket 223. Such positioning ensures later alignment of each pad 300 proximate to the greater trochanters of the user (U).

With both tapered pads 301 and 302 now in place within the compression undergarment 200, one or more compression bands 400 are positioned about the top portion 405 of the compression undergarment 200. Such placement (shown in FIG. 9) can include a single compression band 410 or a plurality of compression band 410-430 dependent upon the level of menstrual cramping and individual preferences of the user (U). In one embodiment, the top edge 411 of the compression bands 400 to cover both the first annular sleeve 210 and corresponding second annular sleeve 220.

Upon assembling the pads 300 into the annular sleeves 210 and 220 of the compression undergarment 200 and securing the compression bands 400, the apparatus 100 is next placed onto the user (U). Some minor adjustments may be necessary for specific placement of both pads 301 and 302 to be located proximate the greater trochanters.

All-in-One Apparatus

It is important to note that the compression undergarment 200 identified in FIG. 1 and FIG. 9 need not include independent components 101, such as tapered pads 300 and compression belts 400. Rather, as shown in FIG. 10, the invention does contemplate use of a single constructed all-in-one apparatus 100. Such system can be a bonded system where the compression belt included sewn in pads 300 with an exterior layer of elastic material sufficient to form and constitute a compression band 400. Alternatively, such apparatus 100 can simply be in the form of a compression undergarment 200 having a sufficient elastic member positioned proximate the greater trochanters of the female user (U).

This undergarment is designed with sufficient built in compression so as to be effective as an independent treatment device or with other apparatus in a manner that it helps maintain the compressive effects of the apparatus and is then used as a post-treatment aid. Even though this undergarment is designed to be used independently of pads, elastic bands or the compression belt, it may be used in conjunction with any of them and then left on as a post treatment. For some, the compressive strength of the undergarment alone may be enough to alleviate the pain associated with menstrual cramping.

It is important to note the apparatus 100, including such compression undergarment 200, can be used as a stand alone device for the relief and treatment of menstrual pain. Alternatively, the apparatus 100 can be used as a post-treatment device for user's (U) suffering from significant menstrual pain subsequent to use of a more robust belt assembly having a strap, one or more pads affixed to the strap and a fastener sufficient to create a compression force about the greater trochanters.

We claim:

1. An apparatus to reduce the effects of menstrual pain, the apparatus comprising:
    a first pad and corresponding second pad both capable of conforming to a female user's hips;
    a compression undergarment having a first annular sleeve and corresponding second annular sleeve, the first annular sleeve receiving the first pad and the second annular sleeve receiving the second pad; and a compression band of sufficient size and dimension to fit around both the first and second pads, the compression band for positioning about the female's greater trochanters and configured to exert sufficient compressive force to compress the greater trochanters to relax ligaments and tendons proximate the female user's uterus.

2. The apparatus of claim 1, wherein each of the first and second pads includes a heat therapy assembly having both a female holder and a removable male heat pad, and wherein the female holder is essentially elliptical and includes an outer ring and a cavity sufficient to receive the male heat pad.

3. The apparatus of claim 2, wherein the male heat pad has a sufficient size and dimension to be locked within the cavity of the female holder, the male heat pad having an exterior sleeve filled with at least one of a gel and a liquid capable of conducting heat.

4. The apparatus of claim 1, wherein the compression undergarment further includes a front side, corresponding back side, first leg portion and second leg portion, and a top portion positioned above the first leg portion and second leg portion connecting both leg portions.

5. The apparatus of claim 1, wherein the interior panel is made from neoprene.

6. The apparatus of claim 1, wherein each of the first and second pads includes an exterior panel and an interior panel, the exterior panel being sufficiently pliable and resilient to conform to a unique shape of the female user's hips while the interior panel is made of a soft and compressible material.

7. A method of relieving the effects of menstrual pain, comprising the steps of:
(a) placing a first pad into a first annular sleeve within a compression undergarment;
(b) positioning a second pad into a second annular sleeve of the compression undergarment; and
(c) fitting the compression undergarment onto a female user such that the first pad and the second pad are positioned proximate the greater trochanters of the user;
(d) securing one or more compression belts over both pads and the compression undergarment; and
(e) compressing, via the compression belt, such that the female user's greater trochanters are compressed to relax ligaments and tendons proximate the female user's uterus.

8. The method of claim 7, wherein the compression undergarment further includes a front side, corresponding back side, first leg portion and second leg portion, such that positioned above the first leg portion and second leg portion is a top portion connecting both leg portions.

9. The method of claim 7, wherein the interior panel is made from neoprene.

10. The method of claim 7, wherein each of the first and second pads includes a heat therapy assembly having both a female holder and a removable male heat pad, wherein the female holder is essentially elliptical and includes an outer ring and a cavity sufficient to receive the male heat pad.

11. The method of claim 10, wherein the male heat pad has a sufficient size and dimension to be locked within the cavity of the female holder, the male heat pad having an exterior sleeve filled with a gel or liquid capable of conducting heat.

12. The method of claim 7, wherein each of the first and second pads includes an exterior panel and an interior panel, the exterior panel being sufficiently pliable and resilient to conform to the unique shape of the female user's hips while the interior panel is made of a soft and compressible material.

13. An apparatus to reduce the effects of menstrual pain, the apparatus comprising:
a compression undergarment wherein the compression undergarment includes a first annular sleeve and a corresponding second annular sleeve, the first annular sleeve dimensioned to be positioned at one side of a female user proximate a greater trochanter, while the second annular sleeve is dimensioned to be positioned at a second side of the female user proximate the corresponding greater trochanter, wherein the compression undergarment further includes a front side, corresponding back side, first leg portion and second leg portion, and a top portion positioned above the first leg portion and second leg portion connecting the first and second leg portions;
a first pad and a corresponding second pad, the first pad fitting into the first annular sleeve and the second pad fitting into the second annular sleeve, wherein each pad includes an exterior panel and an interior panel, the exterior panel being sufficiently pliable and resilient to conform to a unique shape of the female user's hips while the interior panel is made of a soft and compressible material; and
a compression band of sufficient size and dimension to fit around the compression undergarment and both of the female user's hips in addition to the first pad and corresponding second pad, and configured to exert sufficient compressive force to compress the greater trochanters to relax ligaments and tendons proximate the female user's uterus.

14. The apparatus of claim 13, wherein each of the first and second pads includes a heat therapy assembly having both a female holder and a removable male heat pad, and wherein the female holder is essentially elliptical and includes an outer ring and a cavity sufficient to receive the male heat pad.

15. The apparatus of claim 14, wherein the male heat pad has a sufficient size and dimension to be locked within the cavity of the female holder, the male heat pad having an exterior sleeve filled with at least one of a gel and a liquid capable of conducting heat.

16. The apparatus of claim 13, wherein the interior panel is made from neoprene.

17. An undergarment for relieving a woman's menstrual pain, comprising:
a body portion having a waist opening and a leg opening such that the woman can insert her legs into the leg opening and position the waist opening proximate her waist in a worn position;
a compression band substantially circumscribing the body portion such that in the worn position the compression band is positioned about the woman's greater trochanters and compresses the woman's greater trochanters to relax ligaments and tendons proximate the woman's uterus to alleviate pain associated with menstrual cramping.

18. The undergarment for relieving a woman's menstrual pain of claim 17, wherein the compression band is integrally formed with the body portion.

19. A method of relieving a woman's menstrual pain, comprising the steps of:

providing a compression undergarment;

providing a first padded region with the undergarment proximate the woman's first greater trochanter when worn by the woman;

providing a second padded region with the undergarment proximate the woman's second greater trochanter when worn by the woman; and providing a compression means band that compresses the first and second padded regions against the first and second greater trochanters to relax ligaments and tendons proximate the woman's uterus to alleviate pain associated with menstrual cramping.

* * * * *